(12) United States Patent
Hartley et al.

(10) Patent No.: US 8,845,708 B2
(45) Date of Patent: *Sep. 30, 2014

(54) STENT GRAFT INTRODUCER

(75) Inventors: David Ernest Hartley, Subiaco (AU); Krasnodar Ivancev, Lund (SE); Roy K. Greenberg, Bratenahl, OH (US)

(73) Assignees: The Cleveland Clinic Foundation, Cleveland, OH (US); Cook Medical Technologies LLC, Bloomington, IN (US)

( * ) Notice: Subject to any disclaimer, the term of this patent is extended or adjusted under 35 U.S.C. 154(b) by 96 days.

This patent is subject to a terminal disclaimer.

(21) Appl. No.: 11/600,655

(22) Filed: Nov. 16, 2006

(65) Prior Publication Data

US 2007/0123910 A1 May 31, 2007

Related U.S. Application Data

(60) Provisional application No. 60/737,179, filed on Nov. 16, 2005.

(51) Int. Cl.
 *A61F 2/06* (2013.01)
 *A61F 2/954* (2013.01)
 *A61F 2/07* (2013.01)

(52) U.S. Cl.
 CPC ........... *A61F 2/954* (2013.01); *A61F 2002/065* (2013.01); *A61F 2/07* (2013.01)
 USPC ....................................................... 623/1.11

(58) Field of Classification Search
 USPC ........ 606/108, 191, 194, 200; 623/1.11–1.13, 623/1.23; 604/264
 See application file for complete search history.

(56) References Cited

U.S. PATENT DOCUMENTS

| 5,354,279 | A | * | 10/1994 | Hofling | 604/164.12 |
| 5,617,854 | A | | 4/1997 | Munsif | |
| 5,735,811 | A | * | 4/1998 | Brisken | 604/22 |
| 5,776,142 | A | * | 7/1998 | Gunderson | 623/1.11 |
| 6,224,609 | B1 | * | 5/2001 | Ressemann et al. | 606/108 |

(Continued)

FOREIGN PATENT DOCUMENTS

| WO | 0076570 | 12/2000 |
| WO | 2005037141 | 5/2005 |

OTHER PUBLICATIONS

International Search Report from Corresponding PCT application Serial No. PCT/US2006/044494.

(Continued)

*Primary Examiner* — Ashley Fishback
(74) *Attorney, Agent, or Firm* — Brinks Gilson & Lione (57) ABSTRACT

A stent graft introducer has a pusher, a nose cone, a region between the pusher and the nose cone for a stent graft, a sleeve extending over the pusher and proximally to the nose cone to cover the stent graft when retained in the region. An indwelling auxiliary catheter with a pre-curved proximal end is fitted into the introducer. The nose cone has an elongate groove and the auxiliary catheter has its proximal end in the elongate groove. In a partially retracted position of the sleeve the curved proximal end of the indwelling auxiliary catheter is exposed and uncovered by the sleeve and in an advanced position of the sleeve the curved proximal end of the indwelling auxiliary catheter is straightened, extends along the length of the groove in the nose cone and is covered by the sleeve.

13 Claims, 9 Drawing Sheets

(56) References Cited

U.S. PATENT DOCUMENTS

| | | | |
|---|---|---|---|
| 7,537,606 B2 | 5/2009 | Hartley et al. | 623/1.11 |
| 8,012,193 B2 | 9/2011 | Hartley et al. | 623/1.11 |
| 2002/0123698 A1* | 9/2002 | Garibotto et al. | 600/585 |
| 2002/0133217 A1* | 9/2002 | Sirhan et al. | 623/1.11 |
| 2005/0049680 A1* | 3/2005 | Fischell et al. | 623/1.15 |
| 2005/0182476 A1* | 8/2005 | Hartley et al. | 623/1.11 |
| 2005/0234425 A1* | 10/2005 | Miller et al. | 604/508 |

OTHER PUBLICATIONS

Sep. 19, 2007 Non-Final Office Action, U.S. Appl. No. 10/818,538.
Dec. 13, 2007 Amendment and Response, U.S. Appl. No. 10/818,538.
Jan. 17, 2008 Final Office Action, U.S. Appl. No. 10/818,538.
Feb. 14, 2008 Response to Final Office Action, U.S. Appl. No. 10/818,538.
Apr. 1, 2008 Advisory Action, U.S. Appl. No. 10/818,538.
Apr. 1, 2008 Advisory Action, U.S. Appl. No. 10/962,763.
Apr. 15, 2008 Response to Final Office Action, U.S. Appl. No. 10/818,538.
May 23, 2008 Amendment and Response to Election/Restriction, U.S. Appl. No. 10/962,763.
Jun. 5, 2008 Non-Final Office Action, U.S. Appl. No. 10/818,538.
Jul. 8, 2008 Non-Final Office Action, U.S. Appl. No. 10/962,763.
Aug. 14, 2008 Response to Office Action, U.S. Appl. No. 10/818,538.
Oct. 14, 2008 Amendment and Response, U.S. Appl. No. 10/962,763.
Nov. 25, 2008 Final Office Action, U.S. Appl. No. 10/818,538.
Jan. 12, 2009 Final Office Action, U.S. Appl. No. 10/962,763.
Jan. 19, 2009 Response to Final Office Action, U.S. Appl. No. 10/818,538.
Feb. 25, 2009 Response to Final Office Action, U.S. Appl. No. 10/962,763.
Apr. 1, 2009 Advisory Action, U.S. Appl. No. 10/962,763.
Apr. 13, 2009 Response to Advisory Action, U.S. Appl. No. 10/962,763.
May 8, 2009 Non-Final Office Action, U.S. Appl. No. 10/962,763.
Aug. 10, 2009 Amendment and Response, U.S. Appl. No. 10/962,763.
Nov. 18, 2009 Final Office Action, U.S. Appl. No. 10/962,763.
Jan. 11, 2010 Response to Final Office Action, U.S. Appl. No. 10/962,763.
Jan. 26, 2010 Advisory Action, U.S. Appl. No. 10/962,763.
Feb. 8, 2010 Response to Advisory Action, U.S. Appl. No. 10/962,763.
Mar. 2, 2010 Advisory Action, U.S. Appl. No. 10/962,763.
Mar. 24, 2010 Response to Advisory Action, U.S. Appl. No. 10/962,763.
May 10, 2010 Non-Final Office Action, U.S. Appl. No. 10/962,763.
Jul. 16, 2010 Amendment and Response, U.S. Appl. No. 10/962,763.
Oct. 25, 2010 Final Office Action, U.S. Appl. No. 10/962,763.
Nov. 22, 2010 Examiner Interview Summary, U.S. Appl. No. 10/962,763.
Jan. 25, 2011 Response to Final Office Action, U.S. Appl. No. 10/962,763.
Feb. 3, 2011 Advisory Action, U.S. Appl. No. 10/962,763.
Feb. 14, 2011 Response to Advisory Action, U.S. Appl. No. 10/962,763.

* cited by examiner

STENT GRAFT INTRODUCER

CROSS-REFERENCE TO RELATED APPLICATIONS

This application claims priority of provisional application Ser. No. 60/737,179, filed Nov. 16, 2005.

TECHNICAL FIELD

This invention relates to a medical device and more particularly to a medical device adapted for deployment of a stent graft within a human or animal body.

BACKGROUND OF THE INVENTION

This invention will be generally discussed in relation to deployment of a stent graft into an iliac artery where it is necessary to extend a side branch from a stent graft into an internal iliac artery but it is to be understood that the invention is not so limited and may relate to any body lumen in which such a deployment is required.

Throughout this specification the term distal with respect to a portion of the aorta, a deployment device or a stent graft is the end of the aorta, deployment device or stent graft further away in the direction of blood flow away from the heart and the term proximal means the portion of the aorta, deployment device or end of the stent graft nearer to the heart. When applied to other vessels similar terms such as caudal and cranial should be understood.

Stent grafts are used for treatment of vasculature in the human or animal body to bypass a repair or defect in the vasculature. For instance, a stent graft may be used to span an aneurism which has occurred in or associated with the iliac artery. In many cases, however, such a damaged or defective portion of the vasculature may include a branch vessel such as an internal iliac artery. Bypassing such a branch vessel without providing blood flow into it can cause problems and hence it has been proposed to provide a side branch on a stent graft which when deployed is positioned over the opening to the internal iliac artery and then another stent graft can be deployed through the side branch into the internal iliac artery to provide a blood flow path to the internal iliac artery.

Generally, when deploying an endovascular stent graft into a body lumen, it is possible to obtain access to such a body lumen from each end of the lumen where necessary, thereby facilitating placement of a device in the lumen. The internal iliac artery which extends from the common iliac artery below the aortic bifurcation is for all intents and purposes a blind vessel because there is no practical way of performing an endovascular minimally invasive procedure into that vessel other than by entry from the common iliac artery. The term blind vessel is used herein to describe such a vessel.

There have been proposals to deploy a branched stent graft into the common iliac artery via a femoral artery from a femoral incision using the Seldinger technique. Such a branched stent graft has a side arm which is placed to extend into or at least adjacent the internal iliac artery and then a leg extension can be placed through the side arm into the internal iliac artery, however, the use of such devices is very dependent upon favourable layout of the arteries and the ability to obtain access over the aortic bifurcation and in many cases, access is extremely difficult.

It has been proposed to use an indwelling auxiliary catheter positioned in the introducer and through the side arm of the stent graft and when it is deployed to use it to assist with directing a deployment device into the internal iliac artery. To do this it is necessary to snare a guide wire extended from the indwelling auxiliary catheter. This is best done through the contra-lateral iliac artery over the aortic bifurcation. Snaring can be a problem because the guide wire being snared can become entangled around the nose cone of the introducer or the guide wire of the introducer.

This invention proposes an alternative method for enabling access to the internal iliac artery and a deployment device to enable such a method to be practiced.

It is the object of this invention therefore to provide an improved deployment device or at least to provide a physician with a useful alternative.

SUMMARY OF THE INVENTION

In one form, therefore, the invention is said to reside in a stent graft introducer comprising a pusher, a nose cone dilator, a region between the pusher and the nose cone for retention of a stent graft therein, a sleeve extending over the pusher and proximally to the nose cone to cover the stent graft when retained in the region and an indwelling auxiliary catheter comprising a pre-curved proximal end, the nose cone comprising an elongate groove and the pre-curved proximal end of the auxiliary catheter having its proximal end in the elongate groove, wherein in a partially retracted position of the sleeve the pre-curved proximal end of the indwelling auxiliary catheter is exposed and in a curved configuration and not covered by the sleeve and in an advanced position of the sleeve the pre-curved proximal end of the indwelling auxiliary catheter is in a straightened configuration, extends along the groove in the nose cone and is covered by the sleeve.

The term pre-curved is intended to refer to the proximal end of the auxiliary catheter having a curve set into it so that in an unconstrained state the proximal end is curved but that such that in a constrained state the proximal end can be straightened.

Preferably the indwelling catheter extends through the stent graft when retained in the region between the pusher and the nose cone and further wherein the stent graft when retained in the region between the pusher and the nose cone comprises a fenestration in the stent graft and the indwelling catheter extends through the fenestration.

Preferably the indwelling catheter comprises a guide wire therethrough.

Hence it will be seen by this invention that an introducer for a stent graft such as an iliac branched stent graft, can be introduced with the curved catheter straightened along the groove in the nose cone dilator and then when the introducer is adjacent the aortic bifurcation the sleeve can be withdrawn so that the curved catheter takes up its curved configuration again. A guide wire can then be extended to pass down the contralateral iliac artery where it can be snared without the danger of it being entangled with the nose cone or guide wire of the introducer.

The introducer according to this invention can be supplied and sterilized with the sleeve in the retracted position so that the curved proximal end of the indwelling auxiliary catheter remains in its curved configuration but that during introduction the sleeve can be advanced so that the curved catheter is placed into the straightened configuration so that the introducer can be advanced through the vasculature.

In an alternative form the invention comprises an introduction arrangement for a branched stent graft intended for deployment into the lumen of a vessel having a blind vessel extending therefrom; the branched stent graft having a main tubular body having a distal end and a proximal end with a main lumen therethrough, a side arm extending from the main body and having a side arm lumen therethrough and in fluid communication with the main lumen, the introduction arrangement including an introducer, the introducer having a distal end intended to remain outside a patient in use and a proximal end, the proximal end having a nose cone dilator and an arrangement to retain the branched stent graft distally of the nose cone dilator, the nose cone dilator comprising a longitudinal groove thereon, the branched stent graft being retained on the introducer and a sheath on the introducer extending over the branched stent graft to the nose cone dilator, an indwelling catheter having a curved proximal end, the indwelling catheter extending from the distal end of the introducer through an introducer lumen in the introducer to the branched stent graft, exiting from the introducer lumen at a distal end of the branched stent graft and entering the distal end of the side arm through the side arm lumen to the main lumen and extending out of the proximal end of the branched stent graft to the groove in the nose cone dilator, wherein in a partially retracted position of the sleeve the curved proximal end of the indwelling auxiliary catheter is exposed and in a curved configuration and in an advanced position of the sleeve the curved proximal end of the indwelling auxiliary catheter is in a straightened configuration, extends along the length of the groove in the nose cone and is covered by the sleeve, the indwelling catheter having a guide wire extending therethrough, whereby the sheath can be partially withdrawn such that the guide wire can be extended through the curved end of the indwelling catheter before the sheath is fully withdrawn from the branched stent graft.

The means to retain the branched stent graft on the introducer may include trigger wires extending to the distal end of the introducer and release arrangements for separate release of the proximal and distal ends of the stent graft from the introducer. In an alternative form the invention comprises an introducer device and a stent graft retained thereon, the stent graft comprising a tubular body and a fenestration in the tubular body, an indwelling catheter including a curved proximal end and a guide wire extending therethrough and associated with the introducer device, the indwelling catheter extending through the stent graft and the fenestration and to the proximal end of the introducer device whereby the guide wire can be advanced beyond and away from the proximal end of the introducer device via the curved proximal end of the indwelling catheter so that the guide wire can be snared and a deployment device for a side arm can be deployed over the guide wire, once snared, to enter the fenestration.

Preferably the stent graft has a proximal end and a distal end and the indwelling catheter extends outside of the stent graft distally of the fenestration and through the fenestration into the stent graft and towards the proximal end. Such a fenestration can include a side arm extending therefrom. The side arm extending from the fenestration can extend outside or inside the stent graft towards either the proximal or distal ends thereof.

Preferably the stent graft has a proximal end and a distal end and the indwelling catheter extends inside of the stent graft distally of the fenestration and through the fenestration out of the stent graft and towards the proximal end thereof.

In an alternative form the invention comprises an auxiliary indwelling catheter for an introducer, the auxiliary indwelling catheter having a curved proximal end or a proximal end which can be curved such that upon deployment it can be placed into a curved configuration such that a guide wire extended from the catheter can be snared away from the introducer thereby reducing the problem of entanglement of the guide wire with the introducer.

BRIEF DESCRIPTION OF THE DRAWING

This then generally describes the invention but to assist with understanding reference will now be made to preferred embodiments of the invention with the assistance of the accompanying drawings in which.

DETAILED DESCRIPTION

Now looking more closely at the drawings and the first embodiment of stent graft introducer according to the invention.

Figure 1:
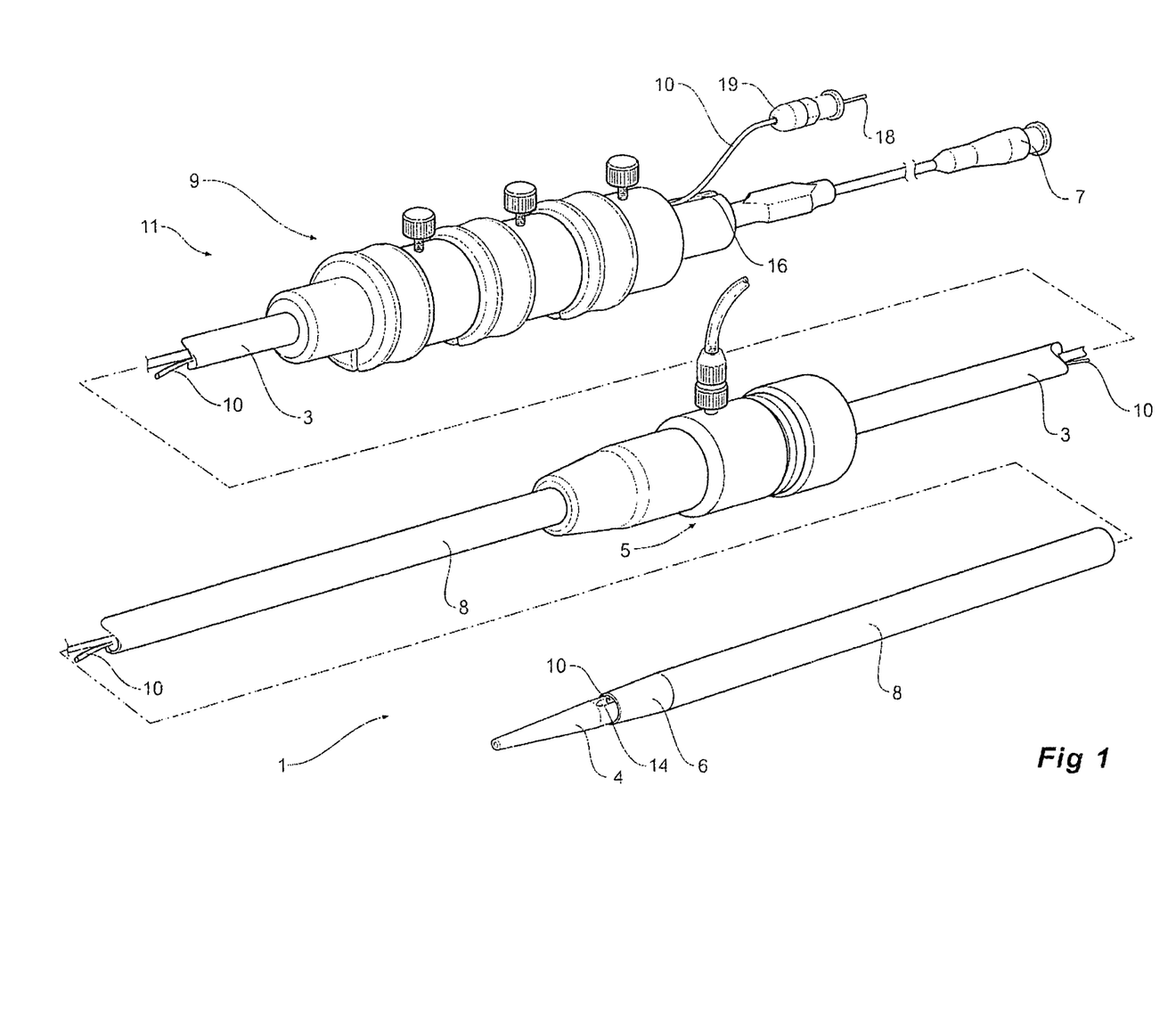
FIG. 1 shows an introducer incorporating an indwelling catheter with a pre-curved proximal end according to one embodiment of the present invention.
Figure 2:
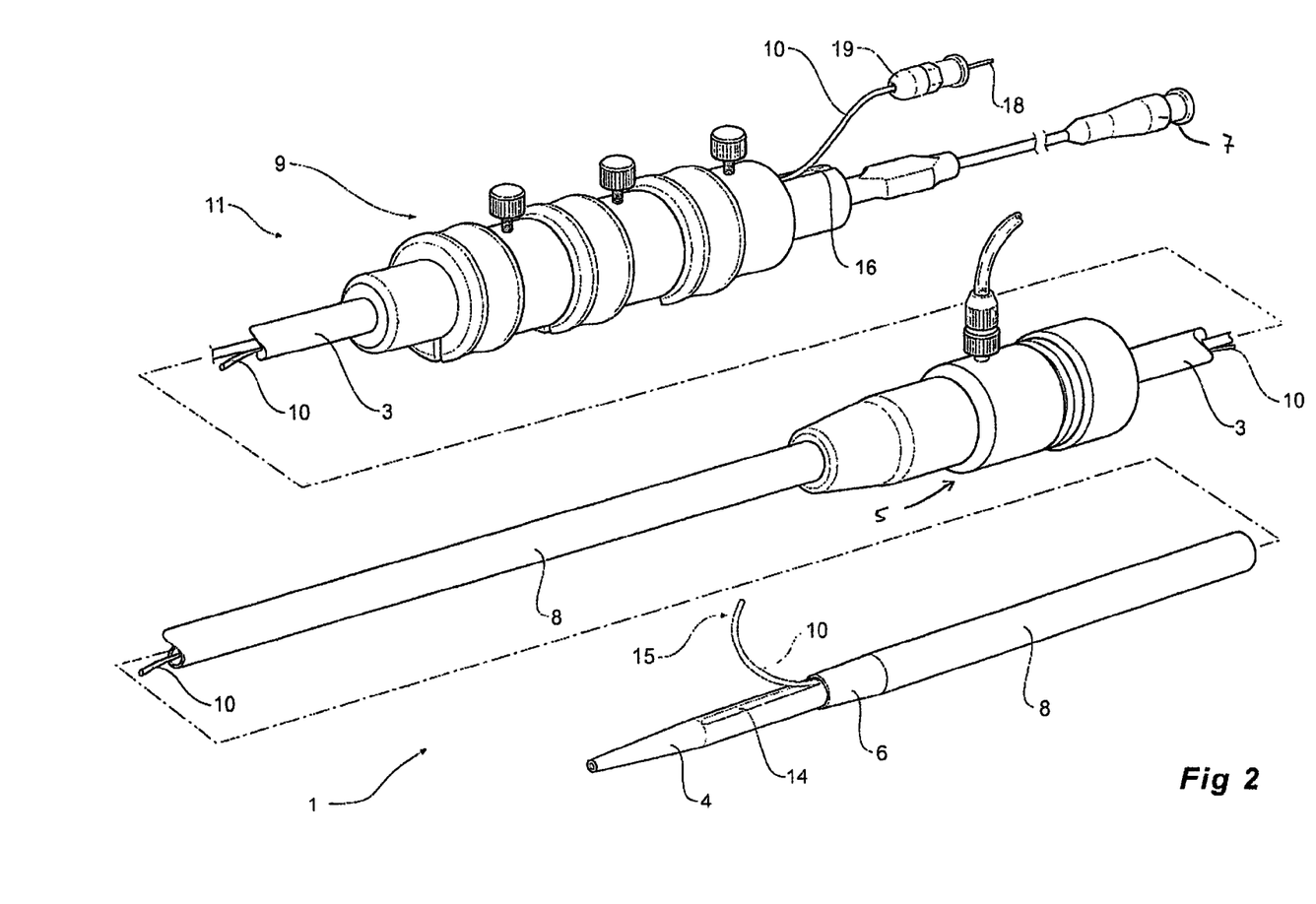
FIG. 2 shows the embodiment of FIG. 1 with the sheath withdrawn to expose the pre-curved proximal end of the indwelling catheter.

FIGS. 1 and 2 depict an introducer 1 having a delivery catheter 3 which extends from a distal handle 11 to a proximal tapered nose cone dilator 4 longitudinally through the passageway of a sheath 8. The introducer sheath extends from a tapered proximal end 6 to a connector valve and manipulator 5 attached about the distal end of the sheath. Connector valve 5 includes a silicone disk (not shown) for preventing the backflow of fluids therethrough. The silicone disk includes a slit for the insertion of the nose cone dilator 4 and delivery catheter 3. The stent graft or implantable device (not shown) is carried on the delivery catheter 3. Connector 5 also includes a side arm to which a polyvinyl tube is connected for introducing and aspirating fluids therethrough. Nose cone dilator 4 includes a tapered proximal end for accessing and dilating a vascular access site over a well-known and commercially available guide wire. Such a guide wire is inserted in a vessel with an introducer needle using, for example, the well-known percutaneous vascular access Seldinger technique. A well-known female Luer lock connector hub 7 is attached at the distal end of the delivery catheter 3 for connection to syringes and other medical apparatus. A set of trigger wire release arrangements generally shown as 9 is on the handle 11 and are used to retain and release a stent graft or implantable device.

The nose cone dilator 4 includes a longitudinal groove 14 in which is received an indwelling catheter 10.

The indwelling catheter 10 extends through a lumen of the delivery catheter 3 to the handle and exits the handle in a groove 16 in the handle 11. The indwelling catheter 10 has an auxiliary guide wire 18 extending through it.

In the advanced position of the sheath 8 as shown in FIG. 1 the pre-curved proximal end 15 (see FIG. 2) of the indwelling catheter 10 has been straightened so that it is in a straightened configuration and extending along the length of the groove 14 in the nose cone dilator 4. In this position, the introducer can be deployed through the vasculature of a patient to a deployment site.

In the retracted position of the sheath 8 as shown in FIG. 2, the sheath 8 has been partially retracted from the nose cone dilator 4 such that the proximal end 15 of the indwelling catheter is exposed and its pre-curved configuration causes it to curve away from the nose cone dilator 4.

Figure 3:
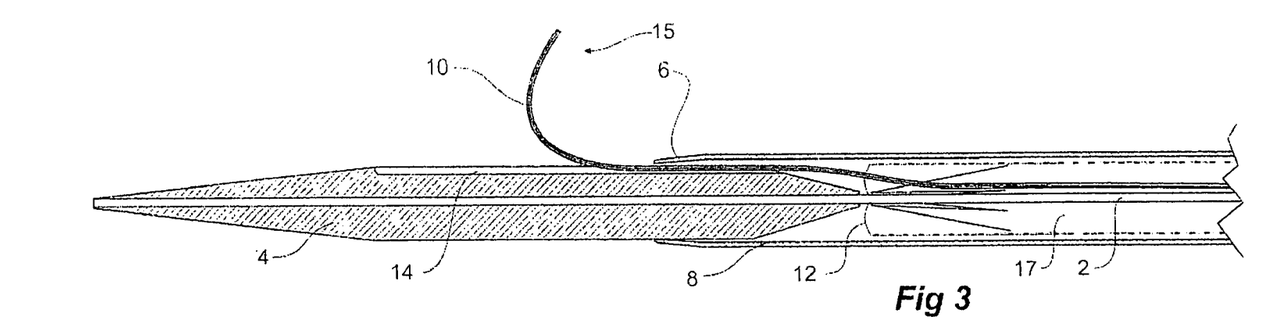
FIG. 3 shows a cross-section of the proximal end of a stent graft introducer incorporating the indwelling catheter of the present invention.
Figure 4:
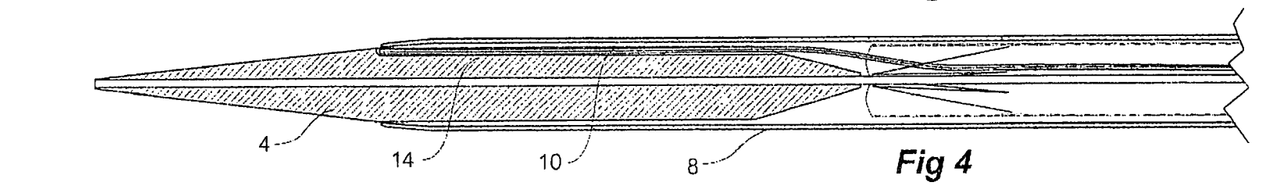
FIG. 4 shows the embodiment of FIG. 3 with the sheath of the introducer advanced.
Figure 5:
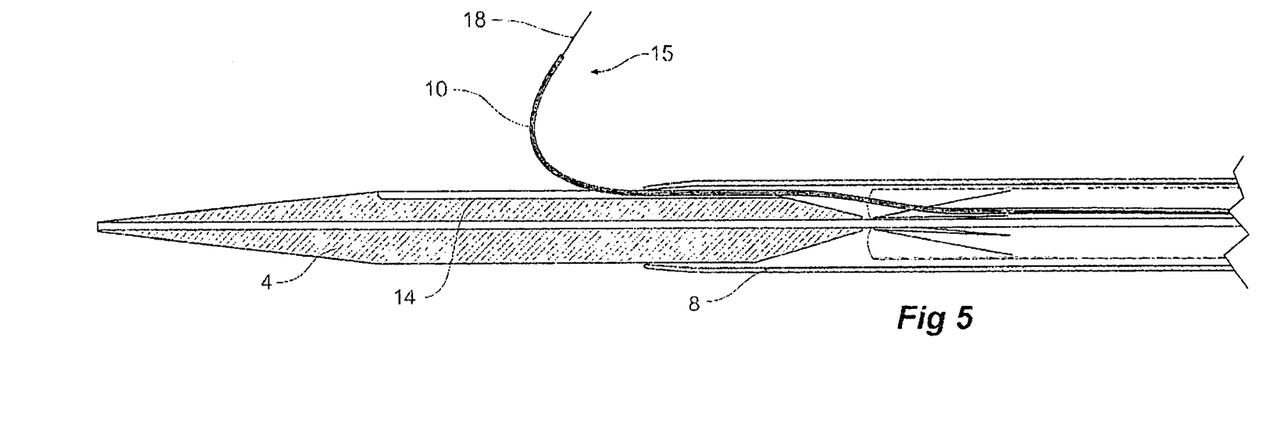
FIG. 5 shows the embodiment of FIGS. 3 and 4 with the sheath retracted so that the curved indwelling catheter takes up its original shape.

Detail of the proximal end of an introducer is shown in cross section in FIGS. 3, 4 and 5. It will be seen that the stent graft introducer has a guide wire catheter 2 extending to a nose cone dilator 4 at the proximal end thereof. A stent graft 17 is retained distally of the nose cone by retention means (not shown) and is covered by the sheath 8. The indwelling catheter 10 extends out of the proximal end 12 of the stent graft 17 and into a groove 14 in the nose cone 4.

In the retracted position of the sheath 8 as shown in FIG. 3, the proximal end 15 of the indwelling catheter 10 is in its curved configuration and is free to curve away from the nose cone dilator 4.

As shown in FIG. 4, the sheath 8 has been advanced to cover a majority of the nose cone dilator 4 and the pre-curved proximal end 15 of the indwelling catheter 10 has been straightened so that it is in a straightened configuration extending along the length of the groove 14 in the nose cone dilator 4. In this position, the introducer can be deployed through the vasculature of a patient to a deployment site.

After the introducer is in a desired position, as will be discussed in relation to FIGS. 6 to 8, the sheath 8 is withdrawn as shown in FIG. 5 so that the indwelling catheter 10 can resume the curved shape of its proximal end 15 so that it is directed away from the nose cone dilator 4. A guide wire 18 can then be advanced to extend from the auxiliary catheter 10 so that it can be snared as discussed below.

Figure 6:
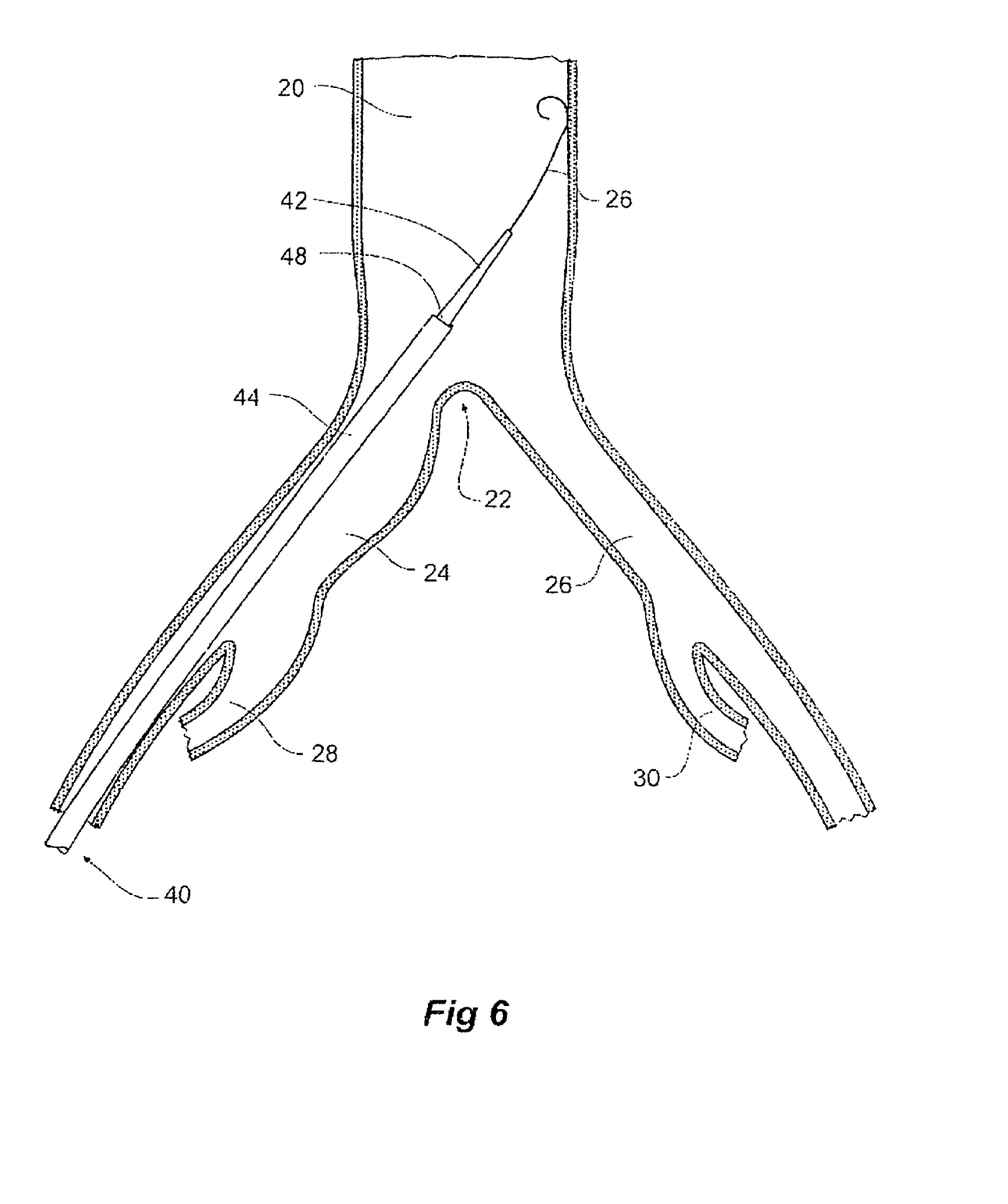
FIG. 6 shows a schematic view of the vasculature of a patient with an introducer deployed into the vasculature.
Figure 7:
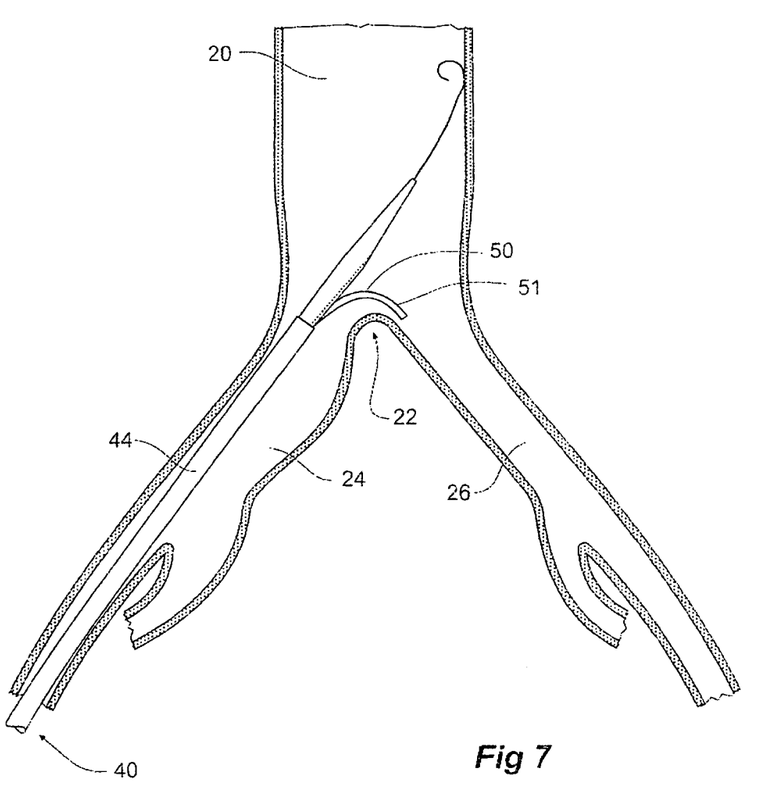
FIG. 7 shows a further stage in the process in which the sheath is retracted to allow the pre-curved proximal end of the indwelling catheter to resume its original shape.
Figure 8:
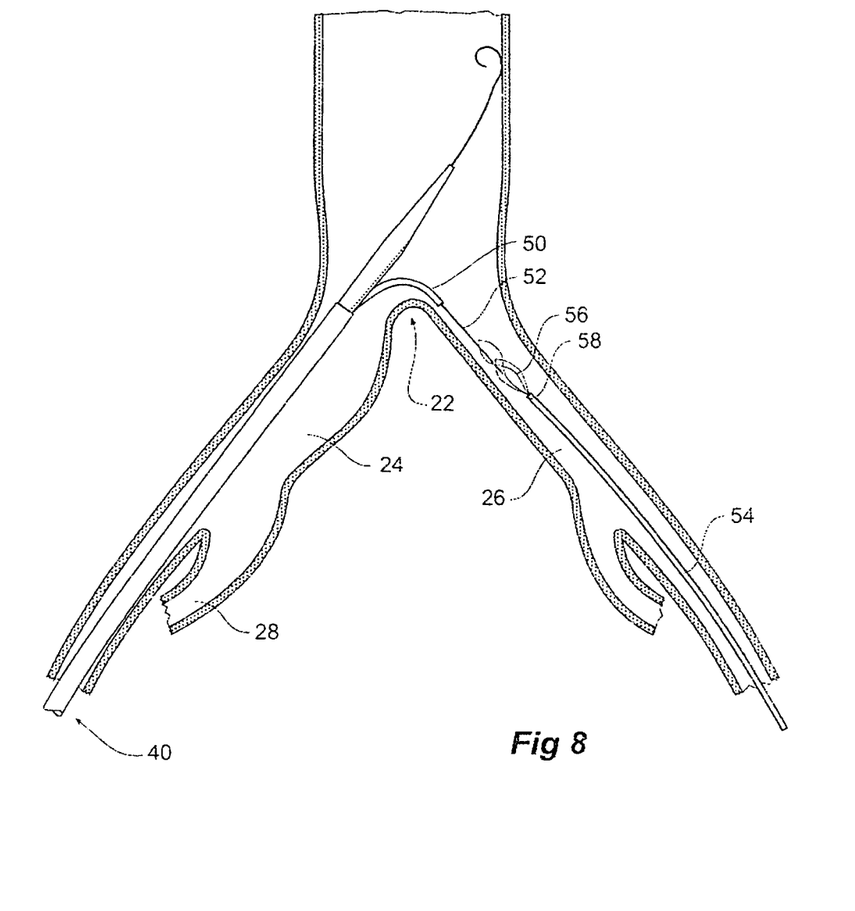
FIG. 8 shows the extension of a guide wire from the indwelling catheter and snaring of the guide wire from the contralateral artery.
Figure 9:
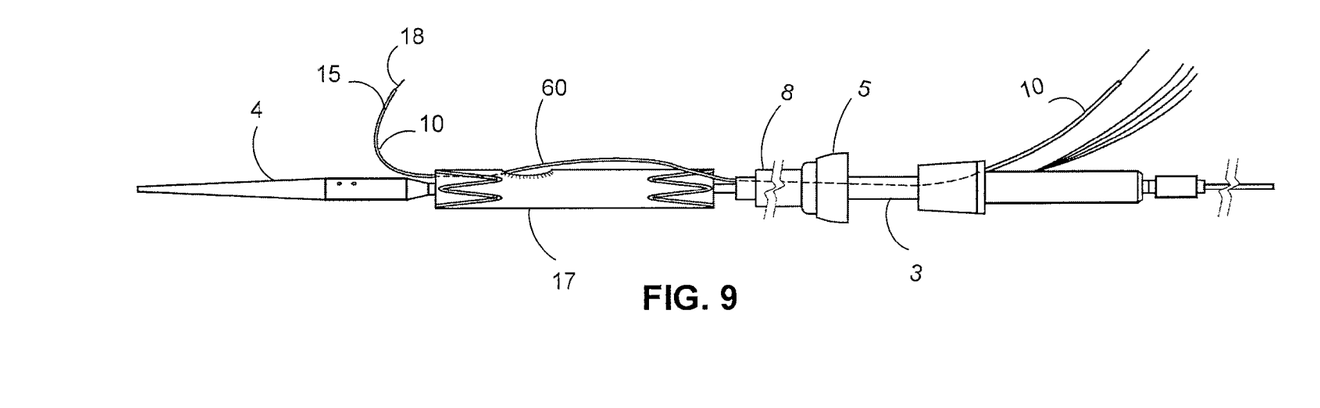
FIG. 9 is a side view of one example of a stent graft having a fenestration formed therein and an indwelling catheter extending outside of the graft distal to the fenestration.
Figure 10:
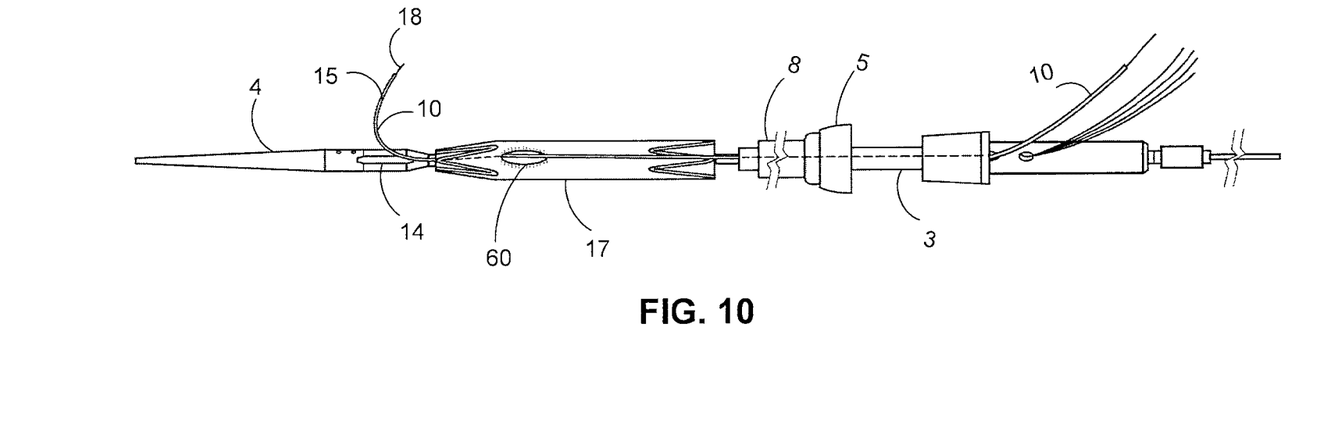
FIG. 10 is a top view of the stent graft illustrated in FIG. 9.
Figure 11:
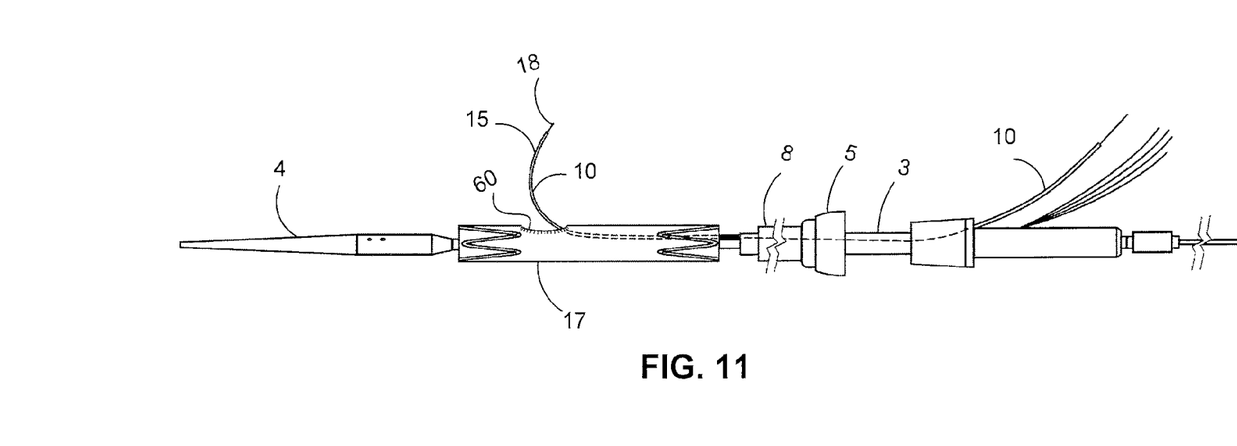
FIG. 11 is a side view of another example of a stent graft having a fenestration formed therein and an indwelling catheter extending inside of the graft lumen distal to the fenestration.
Figure 12:
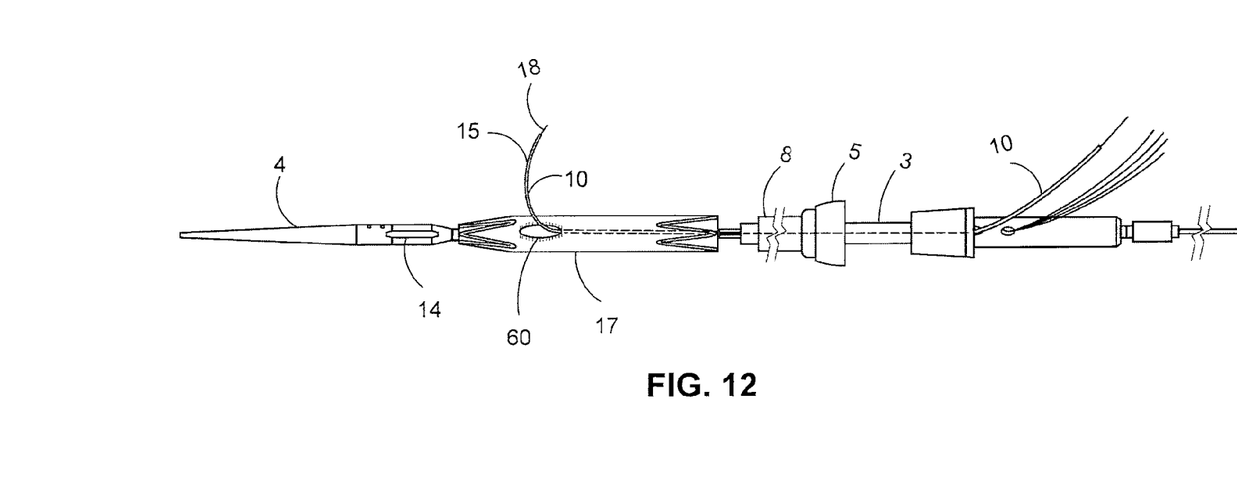
FIG. 12 is a top view of the stent graft illustrated in FIG. 11.
Figure 13:
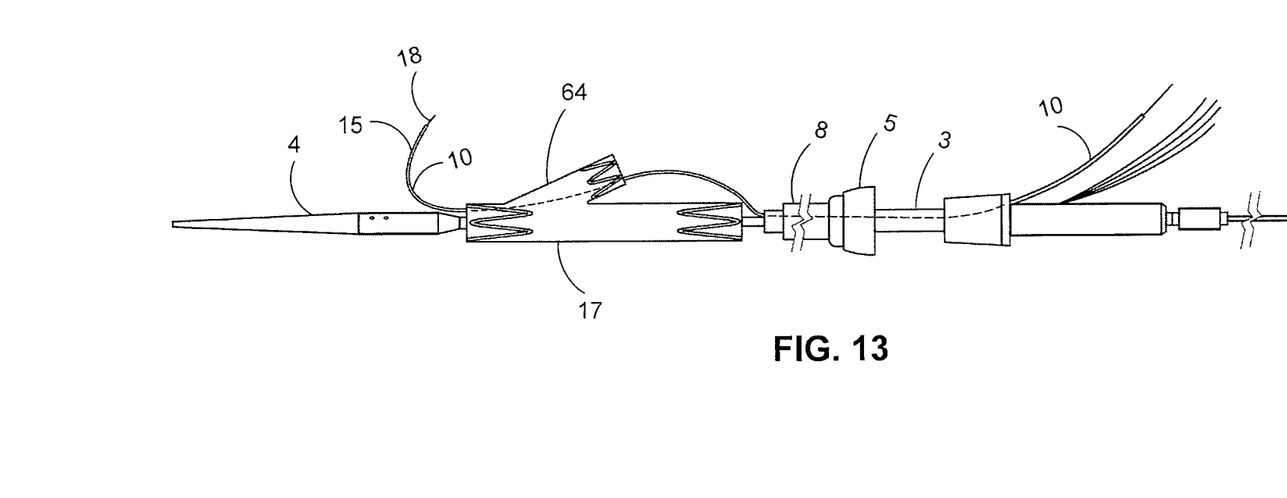
FIG. 13 is a side view of one example of a stent graft having a side arm.

FIGS. 6 to 8 show a schematic view of the vasculature of a patient with an introducer deployed into the vasculature, the process in which the sheath is retracted to allow the curved catheter to resume its original shape and the extension of a guide wire and snaring from the contralateral artery.

FIG. 6 shows schematically part of the vasculature of a patient including an aorta 20 extending down to an aortic bifurcation 22 from which extend iliac arteries 24 and 26. An internal iliac artery 28 extends from the iliac artery 24 and an internal iliac artery 30 extends from the iliac artery 26.

An aneurysm in the iliac artery 24 extends down and includes the opening to the internal iliac artery 28 so that for the deployment of a stent graft into the common iliac artery, it will be necessary to have a fenestration 60 or side arm 64 on the stent graft so that an extension piece can be placed into the internal iliac artery 28. The introducer 40 for such a stent graft includes a nose cone 42 and sheath 44. The introducer 40 as shown in FIG. 4 has been introduced over a guide wire 26 and positioned so that the nose cone is extending up into the aorta 20 and so that the proximal end 48 of the sheath 44 extends past the aortic bifurcation 22.

In the next stage as shown in FIG. 7, the sheath 44 is partially withdrawn so that the proximal end 51 of the indwelling catheter 50 takes up its original curved shape as discussed above in detail in relation to FIG. 5 and in particular, the curved proximal end of the indwelling catheter is directed towards the contralateral iliac artery 26.

As shown in FIG. 8, a guide wire 52 can be extended from the auxiliary indwelling catheter 50 to extend down the contralateral iliac artery and a snare catheter 54 with a snare arrangement 56 at its proximal end 58 can be used to snare the guide wire 52.

In subsequent stages of the deployment of a stent graft into the iliac artery, the sheath can be withdrawn to deploy the stent graft into the iliac artery and a further introducer can be deployed over the guide wire 52 from the contralateral artery to pass through the side arm or fenestration in the stent graft and enable direction of a stent graft into the internal iliac artery 28. PCT Patent Application No. PCT/US2004/033566 (WO 2005/037141) entitled "INTRODUCER FOR AN ILIAC SIDE BRANCH DEVICE" shows methods by which extensions can be placed into such arteries as discussed above and the teaching thereof is incorporated herein by reference in its entirety.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft introducer comprising:
   a proximal end and a distal end,
   a handle at the distal end of the introducer and distal to the delivery catheter, and an elongate groove formed in the handle,
   a nose cone dilator,
   a delivery catheter comprising a proximal end and a distal end, extending from the handle to the nose cone dilator,
   a region between the delivery catheter and the nose cone dilator for retention of a stent graft therein,
   a stent graft disposed on the region,
   a sleeve extending over the delivery catheter and proximally to the nose cone dilator to cover the stent graft when retained in the region, and
   an indwelling auxiliary catheter comprising a pre-curved proximal end and a distal end, the indwelling auxiliary catheter extending from the nose cone dilator, through the delivery catheter, and out of the handle,
   the nose cone dilator comprising an elongate groove thereon and the pre-curved proximal end of the auxiliary catheter having its proximal end in the elongate groove in the nose cone dilator and at least a portion of the distal end of the auxiliary catheter in the elongate groove in the handle, the indwelling auxiliary catheter configured to receive a a guide wire therethrough, wherein when the sleeve is in a partially retracted position the pre-curved proximal end of the indwelling auxiliary catheter is exposed and in a curved configuration and is not covered by the sleeve and when the sleeve is in an advanced position the precurved proximal end of the indwelling auxiliary catheter is in a straightened configuration, extends along the groove in the nose cone dilator and is covered by the sleeve.

2. The stent graft introducer as in claim 1 wherein the indwelling catheter extends through the stent graft when the stent graft is retained in the region between the delivery catheter and the nose cone dilator.

3. The stent graft introducer as in claim 1 wherein the stent graft when retained in the region between the delivery catheter and the nose cone dilator comprises a fenestration in the stent graft and the indwelling catheter extends through the fenestration.

4. An introduction arrangement in combination with a branched stent graft, the branched stent graft intended for deployment into a lumen of a vessel having a blind vessel extending therefrom;
the branched stent graft having a main tubular body having a distal end and a proximal end with a main lumen therethrough, a side arm extending from the main body and having a side arm lumen therethrough and in fluid communication with the main lumen,
the introduction arrangement including an introducer, the introducer having a proximal end, a distal end intended to remain outside a patient in use, a handle assembly at the distal end of the introducer, the handle assembly comprising a handle having an elongate groove, the proximal end having a nose cone dilator and an arrangement to retain the branched stent graft distally of the nose cone dilator, the nose cone dilator comprising an elongate groove thereon, the branched stent graft being retained on the introducer and a sleeve on the introducer extending over the branched stent graft to the nose cone dilator,
an indwelling auxiliary catheter comprising a pre-curved proximal end and a distal end, the indwelling auxiliary catheter extending through at least a portion of the elongate groove in the handle of the introducer through an introducer lumen in the introducer to the branched stent graft, exiting from the introducer lumen at a distal end of the branched stent graft and entering a distal end of the side arm through the side arm lumen to the main lumen and extending out of a proximal end of the branched stent graft to the groove in the nose cone dilator,
wherein when the sleeve is in a partially retracted position the pre-curved proximal end of the indwelling auxiliary catheter is exposed and in a curved configuration and is not covered by the sleeve and when the sleeve is in an advanced position the curved proximal end of the indwelling auxiliary catheter is in a straightened configuration, extends along the length of the groove in the nose cone dilator and is covered by the sleeve, the indwelling auxiliary catheter configured to receive a guide wire extending therethrough, whereby the sleeve can be partially withdrawn such that the proximal end of the indwelling auxiliary catheter is in the curved configuration and the guide wire can be extended through the curved end of the indwelling auxiliary catheter before the sleeve is fully withdrawn from the branched stent graft.

5. The introduction arrangement in combination with a branched stent graft as in claim 4 wherein the arrangement to retain the branched stent graft on the introducer comprises trigger wires extending to the distal end of the introducer and a release arrangement for separate release of the proximal end of the stent graft from the introducer.

6. The introduction arrangement in combination with a branched stent graft as in claim 4 wherein the side arm extends inside the stent graft towards either the proximal or distal ends thereof.

7. The introduction arrangement in combination with a branched stent graft as in claim 4 wherein the side arm extends outside the stent graft towards either the proximal or distal ends thereof.

8. An introduction arrangement in combination with a fenestrated stent graft, the fenestrated stent graft intended for deployment into a lumen of a vessel having a blind vessel extending therefrom;
the fenestrated stent graft having a main tubular body having a distal end and a proximal end with a main lumen therethrough, a fenestration in the main body between the distal end and the proximal end, the fenestration being in fluid communication with the main lumen,
the introduction arrangement including an introducer, the introducer having a proximal end, a distal end intended to remain outside a patient in use, a handle assembly at the distal end of the introducer, the handle assembly comprising a handle having an elongate groove, the proximal end having a nose cone dilator and an arrangement to retain the fenestrated stent graft distally of the nose cone dilator, the nose cone dilator comprising an elongate groove thereon,
the fenestrated stent graft being retained on the introducer and a sleeve on the introducer extending over the fenestrated stent graft to the nose cone dilator,
an indwelling auxiliary catheter comprising a pre-curved proximal end and a distal end, the indwelling auxiliary catheter extending through at least a portion of the elongate groove in the handle of the introducer, through an introducer lumen in the introducer to the fenestrated stent graft, exiting from the introducer lumen at a distal end of the fenestrated stent graft and entering the distal end of the fenestrated stent graft and entering into the main lumen and extending out of the fenestration of the fenestrated stent graft to the groove in the nose cone dilator,
wherein when the sleeve is in a partially retracted position the pre-curved proximal end of the indwelling auxiliary catheter is exposed and in a curved configuration and is not covered by the sleeve and when the sleeve is in an advanced position the curved proximal end of the indwelling auxiliary catheter is in a straightened configuration, extends along the length of the groove in the nose cone dilator and is covered by the sleeve, the indwelling auxiliary catheter configured to receive a guide wire extending therethrough,
whereby the sleeve can be partially withdrawn such that the proximal end of the indwelling auxiliary catheter is in the curved configuration and the guide wire can be extended through the curved end of the indwelling auxiliary catheter before the sleeve is fully withdrawn from the fenestrated stent graft.

9. The introduction arrangement in combination with a fenestrated stent graft as in claim 8 wherein the arrangement to retain the fenestrated stent graft on the introducer comprises trigger wires extending to the distal end of the introducer and a release arrangement for separate release of the a proximal end of the stent graft from the introducer.

10. The introduction arrangement in combination with a fenestrated stent graft as in claim 8 wherein the stent graft has a proximal end and a distal end and wherein the indwelling catheter extends outside of the stent graft distally of the fenestration and enters the stent graft through the fenestration and extends within the stent graft towards the proximal end.

11. The introduction arrangement in combination with a fenestrated stent graft as in claim 8 wherein the fenestration includes a side arm extending therefrom.

12. The introduction arrangement in combination with a fenestrated stent graft as in claim 11 wherein the side arm extending from the fenestration extends inside the stent graft towards either a proximal or distal end thereof.

13. The introduction arrangement in combination with a fenestrated stent graft as in claim 11 wherein the side arm extending from the fenestration extends outside the stent graft towards either a proximal or distal ends thereof.

\* \* \* \* \*

UNITED STATES PATENT AND TRADEMARK OFFICE
CERTIFICATE OF CORRECTION

PATENT NO. : 8,845,708 B2  
APPLICATION NO. : 11/600655  
DATED : September 30, 2014  
INVENTOR(S) : David Ernest Hartley et al.

Page 1 of 1

It is certified that error appears in the above-identified patent and that said Letters Patent is hereby corrected as shown below:

In the Claims

In column 8, claim 9, line 62, after "for separate release of" replace "the a" with --the--.

Signed and Sealed this  
Third Day of March, 2015

Michelle K. Lee  
*Deputy Director of the United States Patent and Trademark Office*